United States Patent [19]
Succi et al.

[11] Patent Number: 5,172,066
[45] Date of Patent: Dec. 15, 1992

[54] METHOD FOR DETERMINING THE END OF USEFUL LIFE OF A GAS PURIFIER AND APPARATUS THEREFORE

[75] Inventors: Marco Succi; Carolina Solcia, both of Milan, Italy

[73] Assignee: SAES Getters SpA, Milan, Italy

[21] Appl. No.: 665,977

[22] Filed: Mar. 7, 1991

[30] Foreign Application Priority Data

Mar. 30, 1990 [IT] Italy .................. 19904 A/90

[51] Int. Cl.$^5$ .................. G01R 27/02; G01N 31/00
[52] U.S. Cl. .................. 324/693; 73/28.01; 73/31.03; 422/98
[58] Field of Search .................. 324/693; 422/82.02, 422/83, 88, 98; 73/28.01, 31.01, 31.03

[56] References Cited
U.S. PATENT DOCUMENTS

| | | | |
|---|---|---|---|
| 2,753,247 | 7/1956 | Greanias et al. | 422/83 |
| 3,805,150 | 4/1974 | Abbe | 324/662 |
| 4,287,751 | 9/1981 | Yasuda et al. | 73/31.05 |
| 4,400,971 | 8/1983 | Tussiker | 73/28.01 |
| 4,472,356 | 9/1984 | Kolesar, Jr. | 422/98 |
| 4,656,832 | 4/1987 | Yukihisa et al. | 73/28.01 |
| 4,674,320 | 6/1987 | Hirshfeld | 73/31.03 |
| 4,795,612 | 1/1989 | Keller | 422/88 |
| 4,911,892 | 5/1990 | Grace et al. | 340/634 |
| 5,008,628 | 4/1991 | Krigmont et al. | 324/693 |

Primary Examiner—Jack B. Harvey
Assistant Examiner—Maura K. Regan
Attorney, Agent, or Firm—David R. Murphy

[57] ABSTRACT

A method, based on the measurement of electrical resistance, and an apparatus for performing the measurement, which indicates the moment in which a gas purifier is about to loose its purification efficiency. The gas purifier can therefore be substituted before the impurity levels in the purified gas output reach undesirably high values.

1 Claim, 3 Drawing Sheets

METHOD FOR DETERMINING THE END OF USEFUL LIFE OF A GAS PURIFIER AND APPARATUS THEREFORE

BACKGROUND OF THE INVENTION

The present invention relates to a method for determining the end of useful life of a gas purifier and an apparatus therefor.

It is known that gases are used in many industrial processes. Some of these processes, such as the manufacture of semi-conductor devices, require that these gases have an extremely high level of purity. Any traces of gas present as an impurity must be held at levels of the order of several parts per billion with respect to the working gas (that is several parts of impurity per $10^9$ parts of working gas).

In order to reach these low levels of impurities there are employed "gas purifiers". In the semiconductor industry there are widely used "inert gas purifiers". By this is intended a purifier of the rare gases He, Ne, Ar, Kr and Xe, as well as $N_2$. Such purifiers of inert gas are described, for example, in United Kingdom patents N° 2,177,079 and N° 2,177,080. See also European patent application publication N° 0,365,490 A 1 in the name of the present assignee.

Although these inert gas purifiers are very efficient in maintaining the levels of impurities of the output gas at the extremely low levels required, at a certain moment they begin to loose their ability to remove the gaseous impurities. The process gas thus becomes less pure and the semiconductor devices produced begin to demonstrate an excessive number of defects and must therefore be rejected. These rejects can be extremely expensive, especially when it is considered that the manufacture of the semiconductor devices requires the employment of techniques utilizing micron or sub-micron technologies.

It is therefore essential to guarantee that the levels of impurities of the process gases employed are below the levels specified.

There are presently known several methods to measure the impurity levels of these working gases. One method is to continually monitor the level of each gaseous impurity present. However this requires extremely specialized equipment and highly qualified personnel. Another method is to measure the quantity of gas which has flown through the purifier and, assuming a known impurity content, to calculate when the gas purifier should start to loose its purification efficiency. Unfortunately the level of impurities of the gas to be purified can vary in an unknown manner thus leading to errors in calculation with the consequence that the purifier may continue to be used even though it has already reached the end of its useful life.

Other methods have been proposed which are based on changes in physical properties of the material which sorbs the impurity gases such as, for example a change of colour.

On the other hand, when the gas purification takes place by means of metallic gettering material, there may be no indication of a colour change.

Italian patent application N° 19012 A/90 filed by the present assignee describes a method for the determination of the end of useful life of an inert gas purifier based on the changes in pressure difference across the purifier, and particularly on an increase of the pressure drop when the purifier nears the end of its useful life, that is to say the purification efficiency is beginning to reach an unacceptable level. Unfortunately this method, based on differences in pressure requires the employment of costly pressure measuring instruments and electronic circuitry, whose use can only be justified on large scale gas purification plants.

When smaller scale gas purification plants having a lower cost are required, whose output of purified gas is less than about 10 1/min, it is necessary to have an equally reliable indication of the approach of end of life but also at a reduced relatively low cost.

BRIEF OBJECTS TO THE INVENTION

It is therefore an object of the present invention to provide an improved method and apparatus for indicating the moment in which a gas purifier, and not necessarily an inert gas purifier, is no longer able to provide the level of purification efficiency required and is free of one or more disadvantages of prior art gas purifiers.

It is another object of the present invention to provide an improved method and apparatus for indicating when a gas purifier is no longer able to provide the level of purification efficiency required, which does not require the use of extremely specialized equipment or highly qualified personnel, without effects due to unknown variations in impurity levels of the gas to be purified, which is not based on physical changes in properties of the material which sorbs the impurities, and that can be measured in an objective manner at reduced cost.

The method according to the present invention, and the relative apparatus, are based on the measurement of the electrical resistance found to exist between an internal point within the gas sorbing material of the purifier and its housing.

Others objects and advantages of the present invention will become clear to the experts in the art by reference to the following description thereof and drawings wherein:

BRIEF DESCRIPTION TO THE DRAWINGS

DESCRIPTION TO THE INVENTION

Materials, such as metals or metallic alloys as loose powders or compressed powders, when they sorb gases undergo transformation of their particles from both a dimensional and chemical point of view. In fact there is generally an increase in particle size with an increase in the volume occupied by the powder. Furthermore the same metal or alloy particles, absorbing gaseous impurities form compounds such as oxides, nitrides, etc. (according to the impurity) and undergo variations in their chemical characteristics. In any case there is an increase in electrical resistance of the gas sorbing material.

It has surprisingly been found that such a variation in electrical resistance can be used to indicate the moment in which a gas purifier is about to reach the end of its useful life. The gas to be purified need not be an inert gas but may be, for example, hydrogen or another gas as the above mentioned effect of electrical resistance depends on the impurities sorbed rather than upon the main gas which flows through the purifier.

The present invention provides an apparatus for the determination of the end of useful life of a gas purifier which has an impure gas inlet in fluid communication with a housing containing a material capable of sorbing gas. Said housing is in fluid communication with a purified gas outlet.

Figure 1:
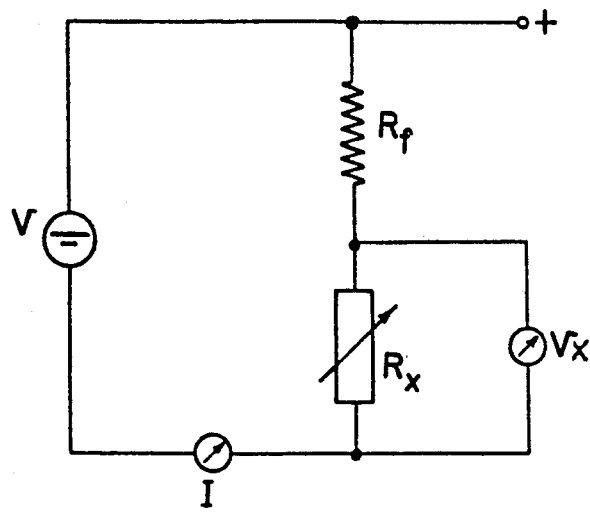
FIG. 1 is a circuit diagram representing the method of the present invention.

As represented in FIG. 1, there is shown a method of the present invention in which the gas sorbing (purification) material is indicated by a variable electrical resistance, whose value increases with increase in the amount of gaseous impurities sorbed. Advantageously the measurement of the resistance can take place, according to the present invention, by measuring the current which flows through the purifier and the potential difference across it until when a fixed voltage is applied between the purifier housing and a fixed point within the gas sorbing material in series with a fixed resistance.

In FIG. 1 $R_f$ indicates the known resistance which limits the current, I, flowing through the gas purifier and $R_x$ the resistance of the purifier which is to be determined. To the system is applied a voltage V, and a potential difference $V_x$ is measured between the gas purifier housing and said fixed point within the gas sorbing material.

When $V = 10_v$ and $R = 141$ ohm, there is the relationship $I (R_x + 141) = V$. From the measurement of I and the potential difference $V_x$ one can obtain the unknown value $R_x$ from one of the following equations:

$$R_x = (V\!:\!I) - R_f \text{ or } R_x = \frac{R_f \cdot V_x}{10 - V_x}$$

In this second case, instead of $V_x$ being measured across the purifier one could measure the potential difference across the fixed resistance $R_f$, taking into account that its value is the complement of $V_x$ with respect to the voltage V.

Figure 2:
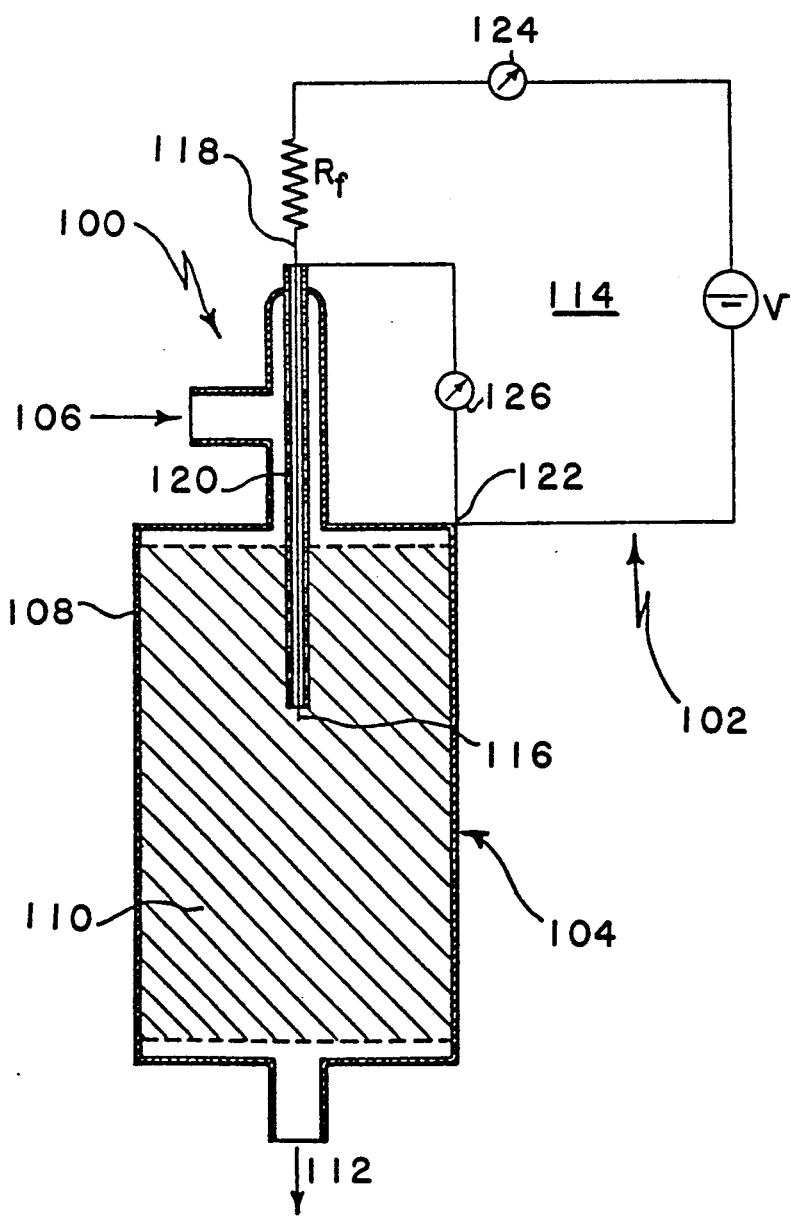
FIG. 2 is a schematic representation of a preferred embodiment of the apparatus of the present invention.

Referring now to FIG. 2 there is shown a schematic representation 100 useful in describing the present invention. There is shown an apparatus 102 for the measurement of the end of useful life of a gas purifier, connected to a gas purifier 104 shown in cross-section. The purifier 104 has an impure gas inlet 106 in fluid communication with a housing 108 which contains a gas sorbing material 110. Housing 108 is also in fluid communication with a purified gas outlet. Apparatus 102 is provided with means 114 which is a circuit for measuring the resistance $R_x$ between housing 108 of purifier 104 and a point 116 within the gas sorbing material 110. Said means 114 comprises a circuit which is a realization of the diagram illustrated in FIG. 1 and uses an electrode 118 isolated from housing 108 by means of an insulating sleeve 120 of ceramic. Between electrode 118 and any part (in the case shown this is represented by 122) of housing 108 there is applied a potential difference by means of a voltage source V through a fixed limiting resistance $R_f$. The measuring instruments may consist, for example, of an ammeter 124 in series to measure the current I, and a voltmeter 126 in parallel to measure the voltage $V_x$.

Applying the relationships given previously with reference to FIG. 1 the value of $R_x$, between point 116 and housing 118, is given.

Figure 3A:
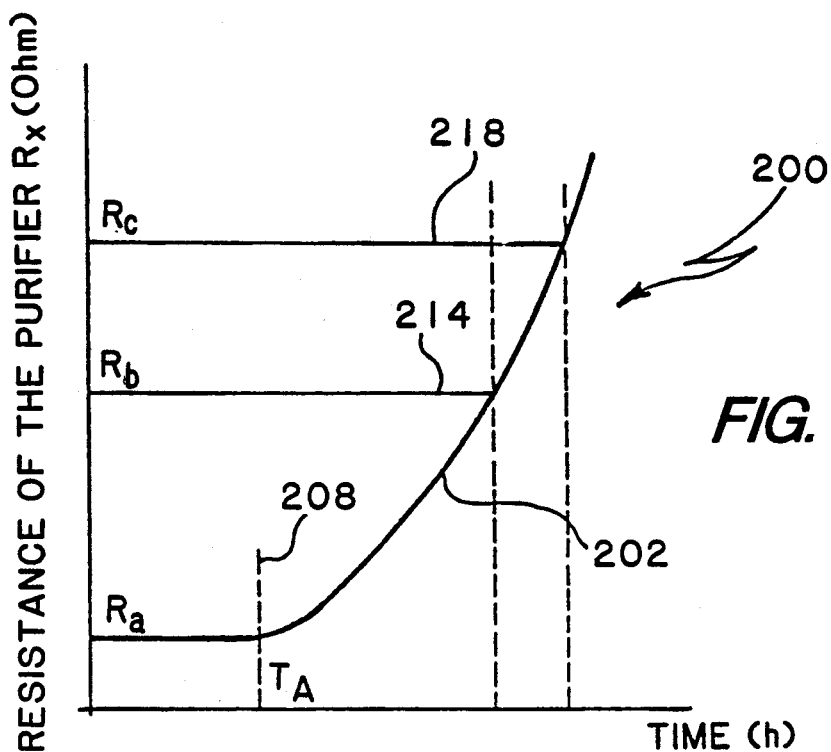
FIG. 3a and 3b are generic representations of the results obtained using the circuit of FIG. 1.
Figure 3B:
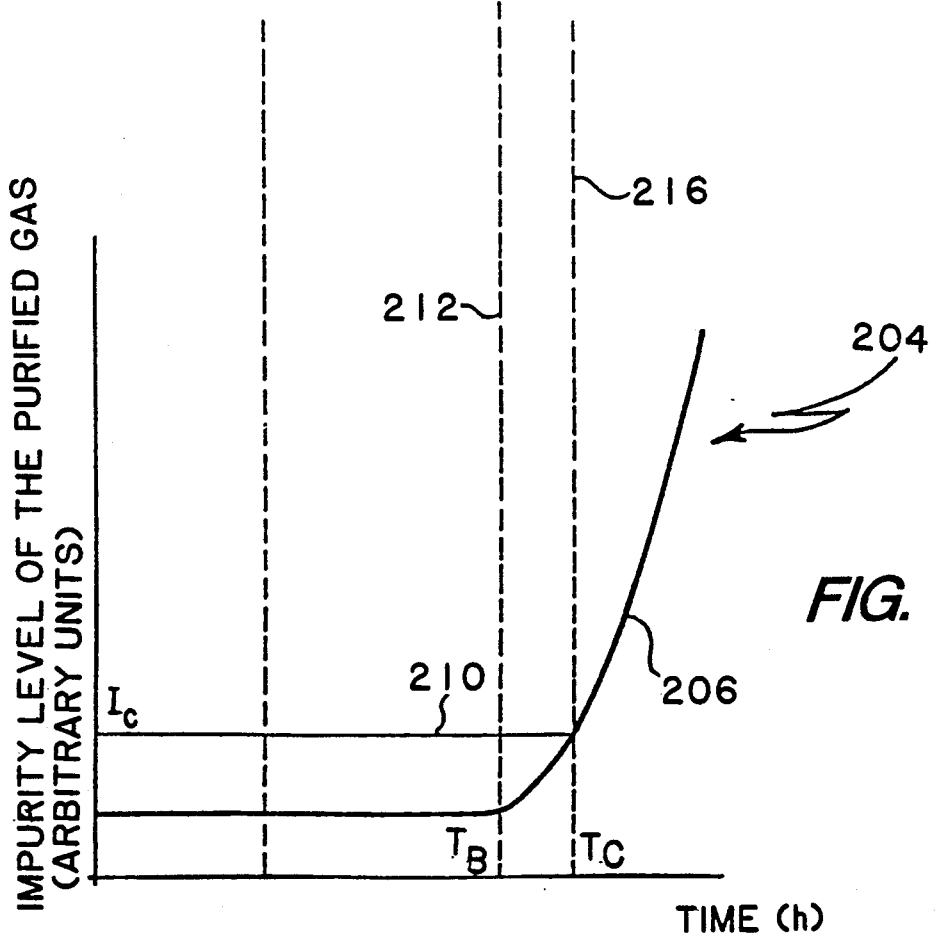

Referring now to FIGS. 3a and 3b there are shown two graphs in which graph 200 gives a curve 202 which indicates the behavior of the electrical resistance $R_x$ during the purification of a gas as a function of time. Graph 204 gives a curve 206 which shows the impurity level of the purified gas at the outlet of the purifier as a function of time.

It is seen from curve 202 that during purification the resistance $R_x$ measured initially remains more or less constant and equal to a value $R_a$ up to time $T_A$ (which corresponds to a quantity $Q_A$ of impurities sorbed) indicated by line 208, above which the electrical resistance measured continuously increases.

As can be seen from curve 206 of FIG. 3b the impurity level of the purified gas remains substantially constant, at a level less than a critical impurity level $I_c$, indicated by line 210, above which the purified gas is considered to be insufficiently pure for the process in which it is being used. However, after time $T_B$ (which corresponds to a quantity, $Q_B$ of impurities sorbed) as indicated by line 212, the level of impurities of the purified gas starts to increase. This takes place corresponding to an electrical resistance $R_b$ indicated by line 214. As more gas is purified to level of impurities of the purified gas continues to increase until it reached the critical value $I_c$ at time $T_c$ (which corresponds to a quantity $Q_c$ of sorbed impurities) as indicated by line 216. This corresponds in its turn to the resistance $R_c$ as indicated by line 218.

Thus when the resistance, between the purifier housing 108 and fixed point 116 within material 110, has reached the value $R_c$ the purifier has reached the end of its useful life.

In practice the means utilized in circuit 114 to measure the value of resistance $R_x$ can be any means capable of giving an indication of its value but it is preferably an ammeter 124 measuring the current in circuit 114 and a voltmeter 126 measuring the voltage $V_x$ between point 116 and housing 108. An electric or electronic device could be used to give a direct indication of the value of $R_x$ is terms of an electric signal or to give an indication when its value reaches a prefixed limiting value $R_x = R_p$ which shows when the purifier has reached the end of its useful life. The signal could be used to activate one or more valves to interrupt the flow of gas which is being purified or to perform any other operation required when the purified has reached the end of its useful life.

It will be understood that the prefixed limiting value of resistance $R_p$ considered as the purification limit of the purifier is equal to the value $R_c$ as determined from FIGS. 3a and 3b. However a value of $R_p$ could be chosen to be less than $R_c$ so as to provide a safety margin and guarantee that the impurity level of the purified gas remains well below the critical impurity level $I_c$. For example a value of $R_p$ could be chosen which satisfies the relationship $R_b < R_p < R_c$. The value of $R_p$ depends on the geometry of housing 108 of the gas purifier, on the physical form of the gas sorbing material 110, on the point 116 where the resistance $R_x$ is measured, as well as other factors, can be measured experimentally.

The method of the present invention to determine the end of useful life of a gas purifier having an impure gas inlet in fluid communication with a housing containing a gas sorbing material, said housing being in fluid communication with a purified gas outlet, includes the steps of measuring the resistance $R_x$ between any predetermined point 116 within the gas sorbing material 110 and the housing 108 of the purifier by any known means, for example, by measurement of current or voltage as previously shown and comparing $R_x$ with a chosen value of $R_p$ and signalling when $R_x > R_p$ in order to indicate that the gas purifier has reached the end of its useful life.

EXAMPLE

A gas purifier in the form of a stainless steel cylinder having an external diameter of 2.5 cm and length 14 cm was filled with 140 g of cylindrical pills of gas sorbing material, each being 3 mm in diameter and 4 mm long. The pills were an alloy of nominal composition 70% Zr - 24.6% V - 5.4% Fe by weight. The purifier was provided with an impure gas tube inlet and a purified gas outlet. A resistance heater was wound round the cylinder and maintained its temperature (and that of the pills) at 400° C. Within the purifier there was inserted a stainless steel wire electrode of 1.2 mm diameter housed in a ceramic tube and connected to a circuit as illustrated in FIG. 2. The value of $R_f$ was 141 ohm and the voltage source was 10 Volts. An ammeter and voltmeter, both commercially available, were connected as illustrated in FIG. 2.

To the purifier inlet was connected a cylinder of argon gas having an impurity content of: $H_2$, 93 ppm; $O_2$, 0.6 ppm; $N_2$, 11.3 ppm; $CH_4$, 10.2 ppm; CO, 10.5 ppm and $CO_2$, 10.3 ppm whose flow rate was $50 \times 10^{-3}$ 1/min.

In order to provide an accelerated life test the argon flow was mixed with a flow at $O_2$ at $031 \times 10^{-3}$ 1/min, corresponding to about 6000 ppm, that is a quantity of impurity which is enormous with respect to the quantities reported above.

Before the accelerated life test, and at intervals during its progress, the flow of $O_2$ at 6000 ppm was stopped and the purification efficiency of the purifier was measured. That is the quantities of each of the gases present in the argon gas flow purified output was measured by a gas chromatograph whose sensitivity ranged from 20 to 100 ppb depending upon the impurity being measured.

Figure 4:
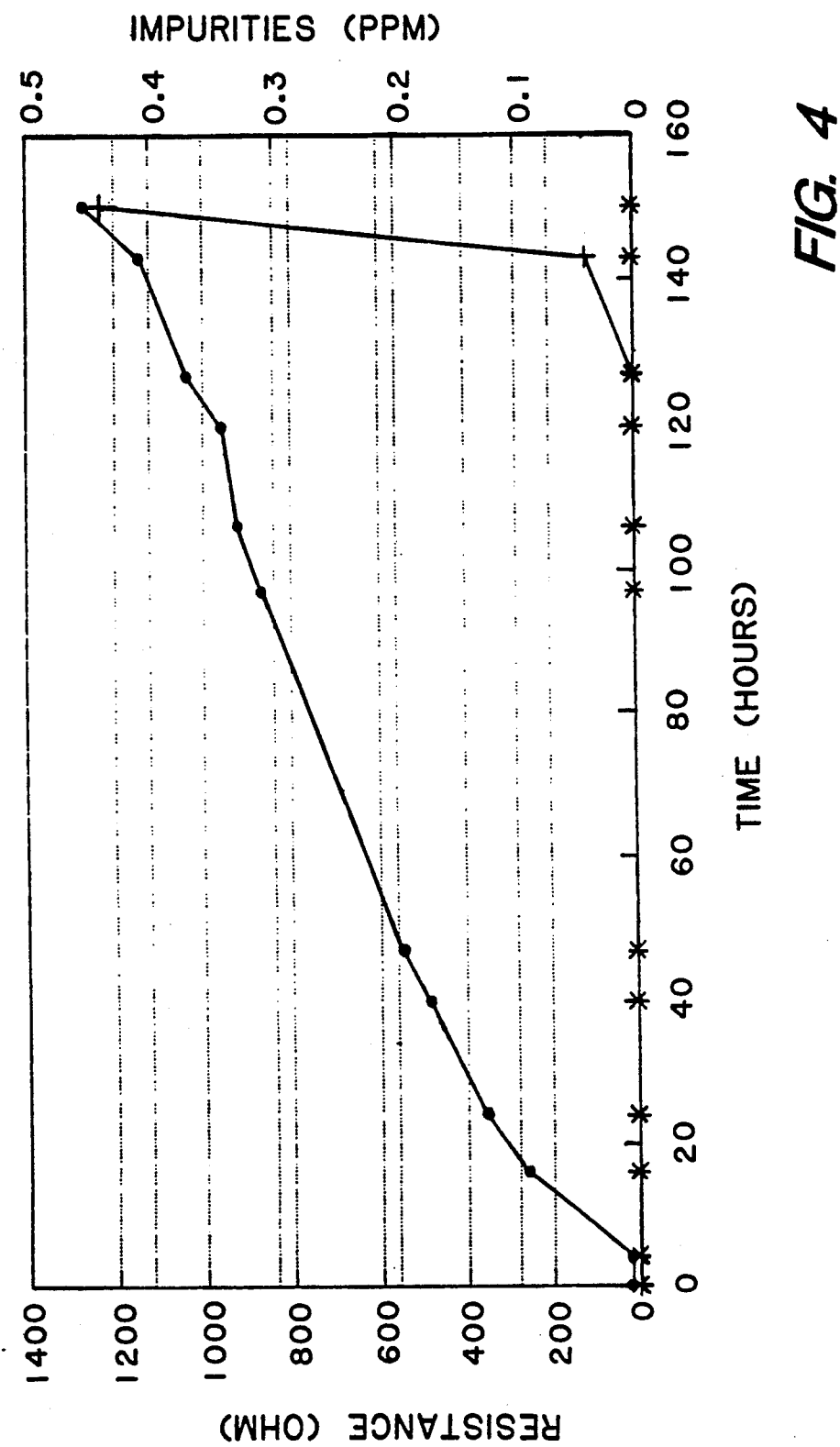
FIG. 4 is a graph which shows the practical results obtained using an apparatus according to FIG. 2, together with an analysis of the purified gases.

FIG. 4 is a curve showing the resistance $R_x$, between the electrode and the purifier housing, experimentally determined as a function of time. There is practically no initial horizontal portion of the curve, as is present in curve 202 of FIG. 3a, because of the enormous quantity of $O_2$ included as an impurity, which caused an almost immediate resistance increase due to sorption. The time $T_A$ as previously defined with reference to FIG. 3a, in this case seems to be less than 5 hours. At the end of the test an increases of resistance $R_x$ of from 0 to 1265 ohm was noted in 150 hours, after sorption of 133 torr-1/g of $O_2$ as measured by the electrode in the gas sorbing material.

Also on FIG. 4 are plotted the results of the impurity gas analyses at the purified gas outlet. For times less than 130 hours (when $R_x = 1050$ ohm) no impurities were detected above the sensitivity limits of the gas chromatograph. At a time of 147 hours the first gas to be detected was $CH_4$ at a level of just under 50 ppb, corresponding to a resistance of $R_x = 1150$ ohm. The next gas to be detected was $N_2$ at about 400 hours. Thus the resistance increase, believed to be only due to oxygen from oxygenated gases, can be related to the amount of oxygen sorbed and knowing when the first gas is detected the value of $R_x$ can be chosen to indicate end of useful life.

Quantitatively different results are obtained with different positions of the electrode but the general behaviour of the curve is similar with a constant increase of resistance measured as a function of $O_2$ sorbed (prevalent with respect to other impurities in this case). The increase of electrical resistance, as defined above, is significant and measurable before the impurities in the outlet gas reach unacceptable levels. A value of resistance an be chosen to indicate the end of useful life when the purifier is furnished with an electrode having fixed characteristics.

Although the invention has been described in considerable detail with reference to certain preferred embodiments designed to teach those skilled in the art how better to practice the invention, it will be realized that other modifications may be employed without departing from the spirit and scope of the invention.

For instances electrode 118 may be inserted on the outlet and of the gas purifier instead of on the inlet end as shown in FIG. 2 and the resistor $R_f$ could be inserted on the other side of the voltage source with respect to the way shown in FIG. 2.

We claim:

1. A gas purifier having an indication of the end of its useful life; said purifier comprising:
   A. an electrically conductive, gas-tight housing; and
   B. an impure gas inlet in fluid communication with the housing; and
   C. a purified gas outlet in fluid communication with the housing; and
   D. a metallic, gas-sorbing material within the housing wherein the gas-sorbing material has the property of increasing its electrical resistance in response to the amount of impurities sorbed; and
   E. means, immersed within the gas-sorbing material, for measuring the electrical resistance of the metallic gas-sorbing material between a point within the gas-sorbing material and the housing;
   wherein the means for measuring electrical resistance comprises a circuit having a voltage source which impresses a voltage between the housing and the point within the gas-sorbing material and means for measuring that voltage and means for measuring the current flowing in the circuit thereby determining the measured resistance of the gas-sorbing material; and
   wherein the point within the gas-sorbing material is at the end of an electrode which passes through the housing but is insulated from the housing by a ceramic insulating sleeve which extends for the complete length of the electrode leaving only the two extremities free; said gas purifier further comprising:
   E. means for comparing the measured resistance with a predetermined value of resistance at which the purifier is at the end of its life.

* * * * *